United States Patent
Girouard

(10) Patent No.: US 6,821,961 B2
(45) Date of Patent: Nov. 23, 2004

(54) MONOUNSATURATED FATTY ACIDS OF AT LEAST 20 CARBON ATOMS AND PERHYDROCYCLOPENTANO-PHENANTHRENE NUCLEUS COMBINATION MOLECULES AND THEIR USE AS WEIGHT-LOSS AGENTS

(76) Inventor: Michael P. Girouard, 18019 Whispering Oaks Dr., Cornelius, NC (US) 28031

( * ) Notice: Subject to any disclaimer, the term of this patent is extended or adjusted under 35 U.S.C. 154(b) by 68 days.

(21) Appl. No.: 10/227,983

(22) Filed: Aug. 26, 2002

(65) Prior Publication Data

US 2003/0114431 A1 Jun. 19, 2003

Related U.S. Application Data

(60) Provisional application No. 60/314,995, filed on Aug. 24, 2001.

(51) Int. Cl.$^7$ ................................................ A61K 31/56
(52) U.S. Cl. ...................................... 514/182; 514/178
(58) Field of Search .................................. 514/178, 182

(56) References Cited

U.S. PATENT DOCUMENTS

| | | | |
|---|---|---|---|
| 3,016,388 A | * | 1/1962 | Duyvene .................... 552/646 |
| 4,005,032 A | | 1/1977 | Haas et al. |
| 4,285,697 A | | 8/1981 | Neary |
| 5,798,348 A | | 8/1998 | Alemany |
| 6,328,910 B1 | | 12/2001 | Askill et al. |

* cited by examiner

Primary Examiner—Barbara P. Badio
(74) Attorney, Agent, or Firm—Garvey, Smith, Nehrbass & Doody, L.L.C.; Seth M. Nehrbass

(57) ABSTRACT

The pharmaceutical and/or cosmetic compositions for treatment of obesity and/or overweight contain an effective amount of a fatty-acid monoester of an estrogen and a fatty acid wherein the estrogen is preferably estrone, diethylstilbestrol, estriol, estradiol or ethinyl estradiol and the fatty acid is eicosenoic acid, especially cis 11 eicosenoic, although cis 5, cis 8, and cis 13 eicosenoic acid are also effective. The C-22 fatty acid monoester of estrogen, cis 13 docosenoic acid (Erucic acid), and the C-24 fatty acid monoester of estrogen, cis 15 tetracosenoic acid (Nervonic acid) are also effective and are included in this disclosure. In addition, synthesized combination molecules formed when a monounsaturated fatty acid of 20 carbon atoms or more is joined via an ester, ether, or amide bond to either a steroid or any molecule containing a perhydrocyclopentanophenanthrene nucleus or perhydrocyclopentanophenanthrene nucleus derivative are also included in this invention. The fatty-acid monoesters mimic the function of estrone monooleate, as a signal that informs the brain of the size of fat tissue mass. In preferred pharmaceutical and/or cosmetic compositions for intravenous injection the monoester is incorporated in a lipidic suspension, prepared from lipoproteins or from liposome components, such as soy oil and egg phospholipids. When administered to rats with a 15% of total adipose tissue, they produce weight reduction of about 10%, by a new and unexpected mechanism. They are useful for the treatment of obesity and/or overweight in mammals, with the advantages of high efficacy and low toxicity.

9 Claims, No Drawings

MONOUNSATURATED FATTY ACIDS OF AT LEAST 20 CARBON ATOMS AND PERHYDROCYCLOPENTANO-PHENANTHRENE NUCLEUS COMBINATION MOLECULES AND THEIR USE AS WEIGHT-LOSS AGENTS

CROSS-REFERENCE TO RELATED APPLICATIONS

Priority of my U.S. Provisional Patent Application, Ser. No. 60/314,995, filed Aug. 24, 2001, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to weight loss. More particularly, the present invention relates to medication-aided weight loss treatments.

2. General Background of the Invention

Since treating patients for weight loss since 1981, the present inventor has observed that roughly seventy-five percent of his patients have little or absolutely no history of overweight or obesity prior to a major event associated with estrogen hormonal changes. The most common estrogen hormonal events are pregnancy (especially second and late pregnancies), hysterectomy, tubal ligation, or peri-menopause/menopause. Usually, the change is dramatic. Interestingly, these patients do not report a change in eating or exercise habits. Furthermore, exercise and strict weight loss produce only modest weight loss in many if not most of these patients, indicating that some aspect of fat metabolism has been altered as a result of the hormonal situations noted above. Because the genetic makeup of these patients has not changed, the present inventor has recognized the role of hormones in producing changes in body fat metabolism in humans.

These observations agree well with what is observed in the literature and current body of knowledge regarding hormones' ability to elicit changes in body fat. Excess production of the hormone cortisol as seen in Cushing's syndrome/disease produces significant truncal obesity which responds poorly if at all to weight loss. A similar situation results from prednisone and other steroid therapy in the human body. Adrenalectomy results in the absence of cortisol and an extreme loss of body fat. Even more significant to the present invention, patients who experience Polycystic Ovary Syndrome (PCOS) secrete huge amounts of the estrogen ESTRONE. Interestingly, these patients do not experience an increase in estrogenic side effects, but do exhibit extreme obesity, poorly responsive to diet and exercise. The role of hormones in eliciting obesity, at least in some, is not questioned. The special role of estrogens is strongly suggested by the inventor's observations.

In U.S. Pat. No. 5,798,348, incorporated herein by reference, Dr. Maria Alemany has demonstrated that certain fatty acid monoesters of estrone are effective in eliciting weight loss and/or treating obesity. The use of fatty-acid monoesters of estrogens (FAME's) for the treatment of obesity and/or overweight has been described wherein the fatty acid components are natural fatty acids designated specifically as the following fatty acids: oleic, linoleic, linolenic, stearic, palmitic palmitoleic, and arachidonic acids.

Oleoyl-estrone (OE) is a naturally occurring fatty acid monoester of estrogen (FAME-ES) that has been shown in numerous published articles to produce rapid and sustained weight loss in a variety of rats. Oleoyl-estrone is just one of a group of naturally occurring fatty acid monoesters of estrogen (FAME-ES). OE produces weight loss whether given via intravenous injection (i.v.), or orally, independent of leptin functionality. Rats given OE reduce their food intake in a dose related manner, while sustaining their energy output, thus resulting in significant and rapid weight loss. In one study, Zucker lean rats lost virtually all their lipid reserves, something that would not be achieved through starvation.

It has been demonstrated that by changing the fatty acid moiety on FAME-ES, the weight loss and appetite suppression effect of the molecule is greatly altered (Life Sciences, Vol. 62, No. 15, pp 1349–1359). To date, the most effective FAME-ES tested has been oleoyl-estrone. However, there are other FAME-ES compounds that have not been tested.

BRIEF SUMMARY OF THE INVENTION

The present invention proposes a new solution to the above-mentioned problem by providing substantially pure new fatty-acid monoesters of estrogens and fatty acids, wherein:

a) the estrogen is selected from the group consisting of estrone, i.e.3-hydroxyestra-1,3,5(10)-trien-17-one; diethylstilbestrol, i.e.4,4'-(1,2-diethyl-1,2-ethenediyl)-bisphenol; estrio, i.e. estra-1,3,5(10)riene-3,16,17-triol, and ethinylestradiol, i.e19-nor-17a-pregna-1,3,5(10)trine-20-yne-3,17-diol;

b) the fatty acid is a mono unsaturated fatty acid containing 20 carbons atoms or more, selected from the group consisting of eicosenoic, docosenoic acid and tetracosenoic acid, and c) in a preferred embodiment, with the proviso that, when the estrogen is steroidal, the acyl group is attached to the hydroxyl group a the c-3 position of the steroid ring system.

In a preferred embodiment, the fatty-acid is eicosenoic acid. In a more preferred embodiment the estrogen is selected from the group consisting of estrone and diethylstilbestrol.

The present invention also provides a substantially pure fatty-acid monoester of an estrogen and a fatty acid, where the estrogen is either estrone, diethylstilbestrol, estriol or ethinyl estradiol; and the fatty acid is either eicosenoic acid, C-22 fatty acid, cis 13 docosenoic acid, or the C-24 fatty acid, cis 15 tetracosenoic.

In addition, the present invention also provides a substantially pure fatty-acid monoester of an estrogen combined with one fatty acid. This fatty acid can either be eicosenoic, docosenoic acid or tetracosenoic acid. Furthermore, the invention provides a substantially pure fatty-acid monoester consisting of estrone monoeicosenoate as well as a substantially pure fatty-acid monoester consisting of diethylstilbestrol monoeicosenoate. The invention also provides a substantially pure fatty-acid monoester where the estrogen is estrone and the fatty acid is cis 11 eicosenoic acid.

In addition, the present invention provides a pharmaceutical and/or cosmetic composition comprising a therapeutically and/or cosmetically effective amount of a substantially pure fatty-acid monoester of an estrogen and a fatty acid, in combination with at least one excipient acceptable for a predetermined administration. The estrogen can be estrone, diethylstilbestrol, estriol, estradiol and ethinyl estradiol and the fatty acid can be eicosenoic acid, the C-22 fatty acid, cis 13 docosenoic acid, and/or the C-24 fatty acid, cis 15 tetracosenoic acid. This pharmaceutical and/or cosmetic composition can be administered via intravenous injection, and the fatty-acid monoester can be integrated in a lipidic suspension. The lipidic suspension can be a lipoprotein suspension. This lipoprotein suspension can be a liposome suspension. Such liposome suspension can be obtained by addition of soy oil and egg phospholipids.

Furthermore, this invention provides a method of lowering body weight in a mammal by administering to the mammal an effective amount of a substantially pure fatty-acid monoester of an estrogen and a fatty acid. The estrogen can be estrone, diethylstilbestrol, estriol, estradiol and ethinyl estradiol, and the fatty acid can be eicosenoic acid, C-22 fatty acid, cis 13 docosenoic acid, or the C-24 fatty acid, cis 15 tetracosenoic acid, in combination with amounts of at least one member selected from the group consisting of pharmaceutically acceptable excipients and cosmetically acceptable excipients in an amount sufficient for the purposes thereof.

In addition, the present invention provides a substantially pure fatty-acid monoester of an estrogen and a fatty acid, wherein the estrogen is selected from the group consisting of estrone, diethylstilbestrol, estriol and ethinyl estradiol; the fatty acid is selected from the group consisting of eicosenoic acid, C-22 fatty acid, cis 13 docosenoic acid, and the C-24 fatty acid, cis 15 tetracosenoic acid, with the proviso that, when the estrogen is steroidal and has a steroid ring system with a C-3 position and a hydroxyl group at the C-3 position, the acyl group of the fatty acid is attached to the hydroxyl group at the C-3 position of the steroid ring system in the fatty acid monoester.

In another embodiment of the invention, molecules are synthesized by combining two different molecules. These molecules are referred to as synthesized combination molecules (SCM). The resulting synthesized combination molecule (SCM), when taken orally, elicits a decrease in appetite and food intake in mammals, while also producing a loss of body weight and/or body fat. These synthesized combination molecules are substantially pure combinations of:

a) a monounsaturated fatty acid molecule of 20 carbon atoms or more, and b) a steroid.

The steroid and fatty acid are joined by an ester, ether, or amide linkage. Preferred fatty acids used in the SCM include the cis isomers of eicosenoic acid (20 carbon, monounsaturated), docosenoic acid (22 carbon, monounsaturated), and tetracosenoic acid (24 carbon, monounsaturated). Other monounsaturated fatty acids of greater than 20 carbons would also be effective. Preferred synthesized combination molecules (SCM's) include the fatty acid monoesters in which the fatty acid is made up of eicosenoic acid, docosenoic acid, or tetracosenoic acid and joined via an ester bond to the steroid estrone. A particularly preferred SCM is the monoester of tetracosenoic acid and the steroid DHEA (dehydroepiandosterone).

In yet another embodiment, the invention provides synthesized combination molecules that are substantially pure combinations of:

1) a monounsaturated fatty acid molecule of 20 carbon atoms or more; and 2) a molecule containing a perhydrocyclopentanophenanthrene nucleus or a modification or derivative of a perhydrocyclopentanophenanthrene nucleus.

An example of a perhydrocyclopentanophenanthrene nucleus is a steroid. In one embodiment, the perhydrocyclopentanophenanthrene exists in the estrogen molecule. The fatty acid and perhydrocyclopentanophenanthrene are joined by an ester, ether, or amide linkage. Such combination molecules are effective in eliciting appetite suppression and a decrease in food intake in mammals, while also producing a loss of body weight and/or body fat. Perhydrocyclopentanophenanthrene is a saturated tetracyclic hydrocarbon, which is the precursor molecule of cholesterol and steroids. Perhydrocyclopentanophenanthrene is also the precursor of Vitamin D.

Suitable excipients include cornstarch, lactose, magnesium stearate, microcrystalline cellulose, pregelatinized starch, and sucrose.

DETAILED DESCRIPTION OF THE INVENTION

The use of the specific fatty acid monoester of estrogen composed of eicosenoic acid and estrogens has not been described, nor would it be expected due to the fact that eicosenoic acid is not generally found in any appreciable amount in mammalian fat tissue. Furthermore, unlike the other fatty-acid monoesters, eicosenoic fatty-acid monoesters of estrogen have been shown by the present inventor to be effective in large mammals and not just rat studies. Thus, the provision of satisfactory new products of the treatment of obesity and/or overweight is still an unresolved problem.

In this specification the term "estrogens" refers to the substances tending to promote estrus and stimulate the development of female secondary sex characteristics. This term comprises natural, semisynthetic and synthetic estrogens, both steroidal and nonsteroidal, such as estrone, diethylstilbestrol, estriol, estradiol, and ethinyl estradiol. In this specification the term "fatty acids" refers to the preferred carboxylic acids for this invention, which eicosenoic, docosenoic acid and tetracosenoic acid.

Dr. Alemany's research published in Life Sci, 1998: 62 (15): 1349–59 demonstrates that the fatty acid moiety hooked to the estrone molecule significantly affects the efficacy. This study shoes that the C-18 saturated fatty acid estrone (stearoyl estrone) is less effective than the C-18 unsaturated fatty acid estrone (oleoyl estrone). Thus, it follows that the C-20 unsaturated fatty acid would be even more effective. Furthermore, in: Horm. Metab. Res. November 1975; 7(6): 467–71, showed that the composition of the free fatty acid fraction differed between the men and women, the female subjects having a lower proportion of saturated fatty acids and higher proportions of oleic and eicosenoic acids. Hence, the article concluded, "The results indicate that the metabolism of polyunsaturated fatty acids in man is influenced by gonadal steroid hormones." This strongly implies 1) the association of eicosenoic acid and oleic acid in the all important area of free fatty acid composition and 2) that this is apparently a function of gonadal steroid hormones, such as estrone. Considering the lower concentration of eicosenoic acid, it is reasonable to assume that on a molar basis, it is significantly more effective than oleoyl estrone.

The present inventor has discovered that the fatty acid monoester of cis 11 eicosenoic acid and an estrogen is also effective in producing weight loss and appears to be significantly more effective than any other fatty acid monoester of estrogen. One study with rabbits showed that when given at a mole/kg dose equivalent to that used for oleoyl-estrone in rats, eicosenoyl estrone (a preferred product) produced 50% greater reduction in appetite and 60% greater weight loss in rabbits than oleoyl-estrone did in rats.

In the present invention, the preferred fatty acid used in the fatty acid monoester of estrogen is eicosenoic acid, especially cis 11 eicosenoic, although cis 5, cis 8, and cis 13 eicosenoic acid may also prove effective. It is also believed that the C-22 fatty acid monoester of estrogen, cis 13 docosenoic acid (Erucic acid), and the C-24 fatty acid monoester of estrogen, cis 15 tetracosenoic acid (Nervonic acid) may also prove effective and are included in this disclosure.

Eicosenoic acid is not a derivative of other fatty acids, but exists uniquely as a separate and significantly different fatty acid, with different chemical properties as identified by standard techniques that show it to be a unique and different molecule. Fatty acid monoesters of estrogens utilizing eicosenoic acid as the fatty acid are also unique and different from other fatty acid monoesters of estrogen (FAME's), exhibiting different efficacy. In fact, research from Dr. Alemany (Life Sci, 1998: 62 (15): 1349–59) shows that simply changing the fatty acid moiety in these FAME's significantly changes the effect of the fatty acid-estrogen monoester. Even fatty acids with equal number of carbon atoms but different degrees of saturation (such as eicosenoic acid and arachadonic acid) yield significantly different effects on appetite and/or weight loss when combined in the fatty acid-estrogen monoester. Therefore, each fatty acid monoester of estrogen is unique, with unique effects, and not derived from another. Monoesters of estrogens and eicosenoic acid are not derived from other fatty acid monoesters, but are synthesized utilizing eicosenoyl chloride and estrogens. In the present invention, estrone is the preferred estrogen.

The preferred pharmaceutical and/or cosmetic compositions of the present invention for treatment of obesity and/or overweight contain an effective amount of the fatty-acid monoester of an estrogen and the fatty acid eicosenoic acid, wherein the estrogen is preferably estrone, diethylstilbestrol, estriol, estradiol, or ethinyl estradiol. A particularly preferred product of this invention is estrone monoeicosenoate. Another particularly preferred product of this invention is diethylstilbestrol monoeicosenoate.

The eicosenoic acid-estrogen monoesters mimic the function of the naturally occurring fatty acid monoester, estrone monooleate, as a signal that informs the brain of the size of fat tissue mass. When administered to rabbits, they produce weight reduction of about 20%, by a) decreasing food intake and b) by a new and unexpected mechanism. Eicosenoic acid-estrogen monoesters are useful for the treatment of obesity and/or overweight in mammals, with the advantages of high efficacy and low toxicity.

As illustrated in the accompanying examples, the new products of this invention can be prepared by reaction between the corresponding estrogen and some activated forms of the corresponding fatty acid (e.g. the acid chloride), in an appropriate solvent (e.g. pyridine), followed by appropriate separation and purification (e.g. by column or HPLC chromatography). Fatty acid monoesters of estrogen behave as a distinct hormone, different from estrone. Apparently, the fatty-acid monoesters of estrogens which are the subject matter of this invention, are products that mimic the hormone activity of estrone monooleate, as a signal that informs the brain of the size of fat tissue mass.

Another aspect of this invention relates to the provision of pharmaceutical and/or cosmetically effective amount of the above-mentioned fatty-acid monoesters of estrogens, and appropriate amounts of excipients suitable for the desired administration of the FAME.

In principle, the compositions of this invention can be administered by standard delivery systems: oral, anal, vaginal, topical, transdermal or parenteral (intravenous, intramuscular or subcutaneous). However, not all the administration routes are equally effective.

Another aspect of this invention relates to the use of a fatty-acid monoester of an estrogen for the preparation of a medicament or formulation for the treatment of obesity and/or overweight in mammals. This use is related to a method of treatment of animal suffering from obesity, and/or cosmetically effective amount of a fatty-acid monoester of an estrogen, together with appropriate amounts of excipients suitable for the desired administration route. In a preferred preparation of this invention, a) the estrogen is selected from the group consisting of estrone, diethyl-stilbestrol, estriol, estradiol, and ethinyl estradiol; b) the fatty acid is selected from the group consisting of eicosenoic, docosenoic acid and tetracosenoic acid and c) with the proviso that the acyl group is attached to the hydroxyl group at the C-3 position of the steroid ring system when the estrogen is steroidal. It is noteworthy that the use (or method of treatment) of the C-3 fatty-acid monoesters of estradiol in the field of obesity/weight reduction is part of this invention.

Eicosenoyl estrone can be characterized as a synthesis of two different molecules: 1) a monounsaturated fatty acid molecule of 20 carbon atoms or more, and 2) a steroid. Thus, other molecules synthesized by combining a monounsaturated fatty acid molecule of 20 carbon atoms or more, and a steroid are also effective and are included in the present invention.

Furthermore, molecules synthesized by combining a monounsaturated fatty acid molecule and perhydrocyclopentanophenanthrene or a derivative or modified perhydrocyclopentanophenanthrene nucleus are also effective and included in the present invention. Perhydrocyclopentanophenanthrene is a saturated tetracyclic hydrocarbon precursor molecule of cholesterol and steroids. Perhydrocyclopentanophenanthrene is also the precursor of Vitamin D. Perhydrocyclopentanophenanthrene also exists in the estrogen molecule. While not wishing to be bound by any particular theory, research suggests that the active part of the steroid molecule in the SCM is actually the perhydrocyclopentanophenanthrene nucleus. Perhydrocyclopentanophenanthrene-containing molecules (such as steroids and particularly estrogen steroids) can produce weight loss when combined with other molecules, such as unsaturated fatty acids, whether this nucleus is saturated or unsaturated, and despite various substitutions on the perhydrocyclopentanophenanthrene nucleus.

EXAMPLE 1

Estrone Eiconsenoate Given at ½ Dose Produces Three Times Greater Weight Loss than Oleyoyl-estrone in New Zealand White Rabbits The present invention demonstrates that the fatty acid monoester of cis 11 eicosenoic acid and estrogen is effective in producing weight loss and appears to be significantly more effective than any other fatty acid monoester of estrogen. One study with rabbits shows that when given at a mole/kg dose equivalent to that used for oleoyl-estrone in rats, eicosenoyl estrone (a preferred product) produced 50% greater reduction in appetite and 60% greater weight loss in rabbits than oleoyl-estrone did in rats.

OBJECTIVE: To test whether the fatty acid monoester of estrogen (FAME-ES) composed of eicosenoic acid and estrone is more effective than the FAME-ES composed of estrone and oleic acid.

DESIGN: Rabbits were given an ad libitum diet of rabbit chow (Purina) with daily determination of rabbit weight and food consumed. During the first 3 weeks, rabbits were only weighed and allowed to eat. On the fourth week, all rabbits were given 0.05 cc dose of peanut oil. For the next ten days, rabbits received either peanut oil (control), OE at a dose of 2 mg/day (3.000 $\mu$mol/day), EE at a dose of 1 mg/day (1.421 $\mu$mol/day), EE at a dose of 0.33 mg/day (0.474 $\mu$mol/day), EE at a dose of 0.2 mg/day (0.284 $\mu$mol/day), or EE at a dose of 0.033 mg/day (0.047 $\mu$mol/day).

SUBJECTS: 5 month old New Zealand white rabbits, initially weighing 3.62–3.3333 kg MEASUREMENTS: Daily determinations of food consumed and body weight.

Materials and Methods

Five New Zealand white rabbits were obtained and caged in their natural environment (outside) and fed a cafeteria, ad libitum diet of rabbit chow. Oleoyl-estrone was obtained from Steraloids, of Rhode Island, at a purity of 81% (HPLC per Dr. Branko Jursic). Estrone-eicosenoate was obtained from Dr. Leroy Morgan at LSU Medical Center, New Orleans, 80% purity (HPLC). Preparations of OE and EE at the proper doses were performed and obtained from Dr. Brian T. Cooper at the Univ. of North Carolina at Charlotte. The appropriate weights of OE or EE were diluted in peanut oil to provide concentrations as follows: 1) OE, 2 mg/0.05 cc; 2) EE, 1 mg/0.05 cc; 3) 0.33 mg/0.05 cc; 4) EE, 0.1 mg/0.05 cc, 5) EE, 0.03 mg/0.05 cc For the initial three weeks, the rabbits were given no medicine or oil. Body weight and food consumed were measured daily; establishing a daily average for food consumed and weight change. All rabbits gained weight during this period. The fourth week, rabbits were given 0.05 cc per day of peanut oil by syringe orally, which they readily accepted without any hesitation or aversion.

Beginning the fifth week, rabbits received an oral dose of OE, EE, or peanut oil as listed in Table 1 below:

TABLE 1

| RABBIT | MEDICINE | DOSE |
| --- | --- | --- |
| #1 | OE | 2 mg/day |
| #2 | EE | 1 mg/day |
| #3 | EE | 0.33 mg/day |
| #4 | EE | 0.2 mg/day |
| #5 | EE | 0.03 mg/day |
| Control | Peanut Oil | 0.05 cc/day |

Rabbits received the assigned dose for 10 consecutive days. Rabbit weight (kg) and food eaten (grams) were determined daily.

Results

Table 2 below shows the initial and final weights for the rabbits, listed according to dose of medicine, along with change in food consumption.

TABLE 2

| RABBIT | INITIAL WT. (kg) | FINAL WT. (kg) | WT. Δ w/ Rx 10 days | WT. Δ Pre-Rx 10 day avg. | FOOD/DAY AVG. PRE-Rx | FOOD/DAY AVG. w/ Rx |
| --- | --- | --- | --- | --- | --- | --- |
| OE, 2 mg/d | 3.70 | 3.60 | −0.10 | +0.121 | 160.55 | 93.8 |
| EE, 1 mg/d | 3.73 | 3.37 | −0.36 | +0.129 | 138.3 | 31.9 |
| EE, 0.33 mg/d | 4.09 | 4.01 | −0.08 | +0.139 | 151.6 | 150.4 |
| EE, 0.2 mg/d | 3.50 | 3.56 | +0.06 | +0.148 | 151.1 | 131.0 |
| EE, 0.03 mg/d | 4.00 | 4.17* | +0.17 | +0.125 | 163.6 | 158.5 |
| CONTROL | 3.96 | 4.10 | +0.14 | +0.139 | 189.5 | 189.5 |

As can be seen from Table 2, both OE and EE elicits weight loss and decreased food consumption in rabbits. However, EE at one half the dose (mg/d) produced more than a three-fold greater weight loss than OE. It is interesting to note that this rabbit also ate approximately ⅓ the amount of food as did the OE rabbit, consistent quantitatively with the degree of weight loss observed.

The rabbit receiving EE at ⅙ the dose of OE also experienced significant weight loss that was only 20% less than that resulting from a much higher dose of OE.

The rabbit receiving EE at 1/10 the dose of OE gained 0.06 kg, however this was less than half the weight gained by the Control rabbit. Obviously, EE exerted an effect even at this low a dose.

The rabbit receiving the dose of EE equal to 1/33 the dose of OE gained more weight than even the control. Interestingly, however, this rabbit lost for the first five days, down to a weight of 3.94 kg. There may have been some brief effect, which was not sustained for some reason.

Thus, oral administration of oleoyl-estrone (OE) and estrone eicosenoate (EE) in all but the lowest dose resulted in weight loss. Interestingly, even though EE was given in less than half the dose of the OE (1 mg/d of EE vs. 2 mg/d of OE), this dose of EE rabbit resulted in 3.6 times more weight loss over a 10-day period.

CONCLUSION: At ½ the dose, estrone eicosenoate produces more than three times the weight loss in rabbits than does OE. EE is more effective on a mol/kg basis than OE in producing weight loss in rabbits Discussion Oleoyl-estrone, a fatty acid monoester of estrogen (FAME-ES), has been shown to cause dose related weight loss in rats when given orally or via i.v. The most likely mechanism of action in causing weight loss is greatly decreased energy intake in the face of sustained energy output. There are many factors which suggest that OE could be a major chemical signal molecule responsible for weight adjustment in the human body: OE is a natural acyl ester found in humans; estrone levels are significantly elevated in obese humans; OE levels in obese humans are significantly lower; OE levels fall in starvation; OE causes lipolysis in human adipocytes.

Published research demonstrates that varying the fatty acid or the estrogen moiety in FAME-ES compounds changes the effectiveness of the molecule in producing weight loss, suppression of food ingestion, or both. This example compares the difference in weight loss and food ingestion suppression effect between orally administered OE and another FAME-ES compound, estrone-eicosenoate (EE). To accentuate the possible greater efficacy of EE, it was given at half the daily dose as OE (g/day). The results were significant, showing that EE at half dose produced weight loss that was 3.6 times greater than that achieved with OE. At other lower doses, EE was also effective in producing either weight loss or reduced weight gain as compared to controls. Only at the lowest dose did EE fail to stop weight gain.

Only one side effect was noted, which may have significance in OE's potential as a weight loss drug for humans. OE was given to the most docile and friendly rabbit. After one week of therapy, this rabbit became very agitated, mean and aggressive, trying on two occasions to bite the handler. Contrary to the aggressive changes seen in the OE rabbit, the EE treated rabbits became very docile and easy to handle. In fact, the most aggressive rabbit pre-treatment, became exceedingly calm, easy to handle and cooperative when given EE in a dose of 0.33 mg/d, In conclusion, FAME-ES compounds produce appetite suppression and weight loss in rabbits in a dose related manner. OE, while effective in promoting weight loss, does appear to produce the unpleasant side effect of irritability and aggressive behavior. By comparison, EE is more effective than OE, producing greater weight loss at a lower dose, with no untoward side effects observed. EE appears to have much greater potential as a weight loss product in humans.

EXAMPLE 2

Greater Effectiveness of Estrone Eicosenoate Over Oleoyl-estrone in Producing Weight Loss in Dogs Subject and Methods Dogs are selected and initial measurements taken. The initial measurements include weight and electrical impedance for each dog as measured by a standard impedance measuring device with electrodes placed between the front and rear paws. The dogs are placed individually in appropriate cages and allowed an ad libitum diet of standard dog chow and water for a 10-day period. Daily measurements include the following:

1. Weight
2. Weight of food consumed
3. Water consumed, both volume and weight

Every other day, the dogs' electrical impedance is measured as an indicator of fat tissue content and loss. The dogs remain confined with out of cage activity or exercise for the duration of the experiment. This initial 10-day period establishes a pattern and average of weight gain, impedance change, and food and water consumption for each dog. The following four days involve giving each dog, orally in the morning, a small bread ball coated with either sugar or syrup and containing 0.6 cc of sunflower oil. This assures the dogs will readily accept the bread ball as a drug delivery device. Should this not occur, the medicines are administered orally in capsule form via gavage tube.

For the next 21 days, dogs receive one of the following:

1. Placebo (3 dogs)
2. Oleoly-estone at a dose of 10 micromoles/kg (4 dogs)
3. Estrone eicosenoate at a dose of 5 micromoles/kg (4 dogs), representing ½ dose of OE dogs
4. Estrone eicosenoate at a dose of 3.33 micromoles/kg (4 dogs), representing ⅓ dose of OE dogs
5. Estrone eicosenoate at a dose of 2.5 micromoles/kg (4 dogs), representing ¼ dose of OE dogs Both Oleoyl-Estrone and Estrone Eicosenoate are prepared by diluting the appropriate weight of each compound in sunflower oil to a standard volume so as to produce various concentrations.

An appropriate volume of either OE or EE is placed into the center of a thick piece of dense sweet bread (non-porous), carefully rolled into a small ball so none of the compound leaks out, and sprinkled on the outer surface with sugar or syrup as determined above. Each dog receives the ball of bread (or capsule gavage) containing the appropriate dose of the appropriate medicine each morning for 21 days. During this 21-day test period, daily measurements are made to determine weight of food consumed, volume and weight of water consumed, and weight change of the dog. Electrical impedance of each dog is measured every other day.

Dogs receiving estrone eicosenoate will experience greater weight loss than dogs receiving oleoyl-estrone. These results of these experiments illustrate the greater efficacy of estrone eicosenoate over oleoyl-estrone in producing weight loss in this large mammal species.

EXAMPLE 3

Human Study Utilizing Estrone Eiconsenoate as an Anti-obesity Drug

SUBJECT AND METHODS a) The required number of subjects are properly screened to fulfill the necessary qualifications,
b) appropriate laboratory evaluation are performed,
c) various aspects of positive drug response in a manner acceptable for drug approval are recorded,
d) adverse drug effects are documented, and
e) patients are adequately followed-up.

OVERVIEW

This study demonstrates that subjects on an ad libitum diet who take estrone eicosenoate:

1. experience a decrease in body fat as measured by weight, waist circumference measurements, and/or body fat or body fat %, and
2. eat less food, and/or
3. experience decreased appetite

GENERAL

In this random, double-blind, placebo controlled study, subjects are selected to one of three groups and take a capsule orally every morning containing one of the following: a) sunflower oil (placebo), b) estrone eicosenoate dissolved in sunflower oil at a dose of 0.75 micromoles/kg, or c) estrone eicosenoate dissolved in sunflower oil at a dose of 0.375 micromoles/kg.

Subjects report weekly for measurements and assessment of any side effects. They are asked to keep a daily record of all food intake, food type, and fluid intake. They are also asked to record any side effects and their frequency (checklist assessment). They are provided with the proper paper work to record these.

SUBJECT SCREENING AND SELECTION

A total of 30 subjects are selected, randomized and placed in one of the three groups: ten subjects receive orally a capsule of sunflower oil for the duration of the study, ten subjects receive orally a capsule of estrone eicosenoate dissolved in sunflower oil every morning at a dose of 0.75 micromoles/kg, and another 10 subjects receive orally a capsule every morning of estrone eicosenoate dissolved in sunflower oil at a concentration of 0.375 micromoles/kg.

QUALIFICATIONS OF SUBJECTS
1) Men between the ages of 18 and 55 with a BMI≧28 are eligible.
2) Women between the ages of 18 and 55, whether menopausal, perimenopausal, or post-menopausal, with a BMI≧28.

SUBJECTS EXCLUDED FROM THE STUDY
People who:
a) are hypothyroid,
b) have a known history of possible estrogen receptive positive cancer (breast, ovarian, uterine, testicular),
c) subjects with a history of anorexia or bulimia,
d) subjects with any history of cancer
e) pregnant females
f) nursing females
g) subjects with EKG's indicating tachycardia, old myocardial infarct, angina, or evidence of coronary artery disease.
h) Subjects with a BMI<28.

Appropriate Laboratory Evaluation
Different tests are performed at least five different times during each study, namely at the screening of potential participants, at the beginning of the study, weekly during the trials, at the end of the first 4 week period and at the end of the second 4 week treatment period.
1) SCREENING: Subjects are screened to exclude hypothyroidism, pregnancy, and heart disease. The following tests can suffice for this: T4, T3, TSH, urine pregnancy test, blood pressure & EKG.
2) BEGINNING OF STUDY: Subject passing the initial screen are evaluated at the beginning of WEEK #1 as follows:
a) Estrone, estradiol, and estriol levels, done on the appropriate day of the menstrual cycle in premenopausal females, and without consideration of the time in the menstrual cycle in all other subjects including men.
b) SMA 20, including glucose, uric acid, and liver function tests
c) Triglycerides
d) Cholesterol, including fractions
e) Glycosalated hemoglobin A1 (HgbA1)
f) Weight, taken on the same scale each time
g) Body fat % and total body fat, determined by bioelectrical impedance device.
   The same instrument must be used on the same patient throughout the study!
h) Height
i) Waist and hip measurements
3) WEEKLY ASSESSMENT: body weight, body fat & body fat %, waist & hip measure
4) END OF WEEK #5 ASSESSMENT: all labs done in step 2 at beginning of study, along with blood pressure, TSH and T4, T3 and rT3.
5) END OF WEEK #11: same as in #4, but also include EKG.
6) END OF WEEK #13: same as listed in step 4 above.
7) END OF WEEK #18: same as step 5.
8) END OF WEEK #20: (optional; include if deemed important) same as step 4.

Subjects selected to participate in the studies have the following initial measurements: WEIGHT, WAIST to HIP RATIO, HEIGHT, BMI (calculated), BODY FAT % & TOTAL BODY FAT (via bioelectrical impedance method). Criteria for participation in the studies are listed below.

STUDY DESIGN
Subjects selected for participation are allowed an ad libitum diet and are given an evaluation sheet to assess their appetite and food intake. Foods excluded include alcohol. Low calorie liquids are stressed in place of high calorie liquids such as fruit juices, milk, sweet tea (tea with sugar), regular soft drinks, coffee with sugar, etc. The importance of drinking 8 glasses of low calorie liquids per day is stressed.

DURATION
The study can be divided into the following periods:
1) WEEK #1—A DAILY assessment of appetite and food intake is made for one week prior to any medication being issued. This is done by having the patient fill out a hunger questionnaire and by keeping a record of food intake. Food intake record should include amount, type, frequency and time ingested.
2) WEEKS #2, 3, 4, & 5—A four week period where subjects are given a weeks supply of medication at the once weekly weigh-ins. Subjects are split into three groups:
   a) One group receives placebo.
   b) One group receives an appropriate dose of EE equal to 0.75 μmol/kg q AM with food.
   c) The third group receives an appropriate dose of EE equal to 0.75 μmol/kg q AM with food.
Ad libitum diets are followed, and food intake and appetite are assessed daily by the patient with an appropriate questionnaire and booklet. Weekly check-ins for weight and other measurements are done.
3) WEEKS 6 & 7—all subjects are given a drug holiday; weekly revisits for measurements continue.
4) WEEKS 8, 9, 10 & 11—Medication resumes, each group receiving the same medication they received during weeks 2–5.
5) WEEKS 12 & 13—No medication. Just weekly reassessment.
6) WEEKS 14–18—Placebo group only, given 4 weeks of medication in a dose yet to be determined. Weekly assessments to occur as usual.
7) WEEK 18 & 22—Original medication groups are evaluated for weight, body fat and %, and waist measurements. Subjects should be blind to all measurements.

OUTCOME
This study demonstrates that EE 1) reduces appetite, and does so in a dose-dependent manner, and/or 2) produces weight loss, loss of body fat, and/or decrease of body fat % as determined by the various measurements in the study.

EXAMPLE 4

The Effectiveness of Synthesized Combination Molecules (SCM) in Producing Decreased Food Consumption, Weight Loss, and/or Body Fat Loss in Rats when the Synthesized Combination Molecule Consists of a Monounsaturated Fatty Acid Molecule of 20 Carbons or more Joined by an Amide, Ester, or Ether Linkage to a Steroid Molecule.

Introduction
Certain molecules are synthesized by combining two different molecules: 1) a monounsaturated fatty acid molecule of 20 carbon atoms or more, and 2) a steroid. These new molecules vary as to the connecting bond, which can be an ester, ether, or amide linkage. The resulting synthesized combination molecule (SCM), when taken orally, elicits a decrease in appetite and food intake in mammals, while also producing a loss of body weight and/or body fat.

Subject and Methods

Osborne Mendle rats are selected as the study subjects due to their propensity to gain fat when fed a high fat diet. An initial measurement of body weight is performed on each rat. The rats are placed individually in appropriate cages and allowed an ad libitum diet of standard rat chow and water for a 10-day period. During this 10-day period the rats are gavaged daily with 0.1 cc volume of sunflower oil to allow them to become comfortable with being handled and receiving the gavage tube (it takes about 10 days for this acclimation to occur, and is important so that the animals are not stressed by the gavage).

Daily measurements include the following:
1. Weight
2. Weight of food consumed
3. Spillage
4. Water consumed, both volume and weight The rats remain confined and are denied out-of-cage activity or exercise for the duration of the experiment other than normal daily activity confined to the cage. This initial 10day period establishes a pattern and average of weight gain, to acclimate the animals to the gavage procedure, and determine the average food and water consumption for each rat.

For the next 28 days, rats receive 0.1 cc volume of either placebo (sunflower oil) or one of several synthesized combination molecules (SCM's) consisting of 1) a monounsaturated fatty acid containing 20 carbon atoms or more joined to 2) a steroid molecule, in which the linkage between the fatty acid molecule and the steroid molecule is an amide, ester, or ether bond. Specific SCM's tested include the monoester of tetracosenoic acid and the steroid DHEA (dehydroepiandosterone). Preferred fatty acids used in the SCM include the cis isomers of eicosenoic acid (20 carbon, monounsaturated), docosenoic acid (22 carbon, monounsaturated), and tetracosenoic acid (24 carbon, monounsaturated). Preferred synthesized combination molecules (SCM's) include the fatty acid monoesters in which the fatty acid is made up of eicosenoic acid, docosenoic acid, or tetracosenoic acid and joined via an ester bond to the steroid estrone. In this study, three SCM's will be tested simultaneously:

FIRST SCM: the monoester of tetracosenoic acid and the steroid dehydroepiandosterone (DHEA).

SECOND SCM: the monoether of tetracosenoic acid and the steroid DHEA.

THIRD SCM: the monoester of eicosenoic acid and the steroid DHEA.

Rats are assigned to each study group and receive the prescribed SCM as follows:
1. Placebo as sunflower oil, 0.1 cc volume (10 rats/SCM).
2. One of the three SCM's described above, at a dose of 10 micromoles/kg (10 rats/synthesized combination molecule [SCM]).
3. One of the three SCM's described above as described above at a dose of 5 micromoles/kg (10 rats/synthesized combination molecule [SCM]).
4. One of the three SCM's described above as described above at a dose of 3.33 micromoles/kg (10 rats/synthesized combination molecule [SCM]).
5. One of the three SCM's described above as described above at a dose of 2.5 micromoles/kg (10 rats/synthesized combination molecule [SCM]).

The synthesized combination molecule (SCM) preparations to be administered to the rats are prepared by diluting the appropriate weight of each synthesized combination molecule (SCM) in sunflower oil to a standard volume so as to produce the appropriate concentration as noted above for each study group, and so as to allow the prescribed daily dose to equal 0.1 cc.

An appropriate volume of the synthesized combination molecule (SCM) is administered via oral gavage of the appropriate dose each morning for 28 consecutive days. During this 28day test period, daily measurements continue to be made to determine weight of food consumed, volume and weight of water consumed, and weight change of the rat.

At the end of the study, rats are anesthetized then sacrificed via guillotine. Blood is collected by direct cardiac puncture, and determinations made of the following blood and plasma parameters including a chemistry panel with lipids which includes glucose, triacylglycerols, urea, and insulin. A CBC is also performed. Measurements to determine loss of fat tissue in the rat's fat pad are also performed. Weight of the uterus is determined. The rats' intestines are then cleaned, the rats are re-weighed, and the whole rat is placed in a blender and made a smooth paste. The paste is used to determine lipid, energy, and water content.

This results of this study show the efficacy of these SCM in producing 1) a reduction in food consumption, and/or, 2) a reduction of body weight &/or body fat, in a statistically significant manner.

EXAMPLE 5

Human Study Demonstrating the Effectiveness of Synthesized Combination Molecules (SCM) in Producing Decreased Food Consumption, Weight Loss, and/or Body Fat Loss in Humans when the Synthesized Combination Molecule Consists of a Monounsaturated Fatty Acid Molecule of 20 Carbons or more Joined by an Amide, Ester, or Ether Linkage to a Steroid Molecule

INTRODUCTION

Certain molecules are synthesized by combining two different molecules: 1) a monounsaturated fatty acid molecule of 20 carbon atoms or more and 2) a steroid molecule. These new molecules vary as to the connecting bond, which can be an ester, ether, or amide linkage. The resulting synthesized combination molecule (SCM), when taken orally, elicits a decrease in appetite and food intake in humans, while also producing a loss of body weight and/or body fat.

Subject and Methods
f) The required number of subjects are properly screened to fulfill the necessary qualifications,
g) appropriate laboratory evaluation are performed,
h) various aspects of positive drug response in a manner acceptable for drug approval are recorded,
i) adverse drug effects are documented, and
j) patients are adequately followed-up.

Overview

The study demonstrates that subjects on an ad libetum diet who take an SCM:
1. Experience a decrease in body fat as measured by weight, waist circumference measurements, and/or body fat or body fat % determinations, and
2. Eat less food, and/or
3. Experience decreased appetite.

General

In this random, double-blind, placebo controlled study, subjects are selected to one of three groups and take a capsule orally every morning containing one of the following: a) sunflower oil (placebo), b) a specific SCM as described above, dissolved in sunflower oil at a dose of 0.75 micromoles/kg, or c) a SCM dissolved in sunflower oil at a dose of 0.375 micromoles/kg.

One of several synthesized combination molecules (SCM's) consisting of 1) a monounsaturated fatty acid containing 20 carbon atoms or more joined to 2) a steroid molecule, in which the linkage between the fatty acid molecule and the steroid molecule is an amide, ester, or ether bond. Specific SCM's tested include the monoester of tetracosenoic acid and the steroid DHEA (dehydroepiandosterone). Preferred fatty acids used in the SCM include the cis isomers of eicosenoic acid (20 carbon, monounsaturated), docosenoic acid (22 carbon, monounsaturated), and tetracosenoic acid (24 carbon, monounsaturated). Preferred synthesized combination molecules (SCM's) include the fatty acid monoesters in which the fatty acid is made up of eicosenoic acid, docosenoic acid, or tetracosenoic acid and joined via an ester bond to the steroid estrone. In this study, three SCM's will be tested simultaneously:

| | |
|---|---|
| FIRST SCM: | the monoester of tetracosenoic acid and the steroid DHEA |
| SECOND SCM: | the monoether of tetracosenoic acid and the steroid DHEA. |
| THIRD SCM: | the monoester of eicosenoic acid and the steroid DHEA. |

Subjects report weekly for measurements and assessment of any side effects. They are asked to keep a daily record of all food intake, food type, and fluid intake. They are also asked to record any side effects and their frequency (checklist assessment). They are provided with the proper paper work to record these.

Subject Screening and Selection

A total of 90 subjects are selected, randomized and placed in one of three SCM study groups based on the three SCM's above. For each of the three SCM groups, subjects are assigned as follows: ten subjects receive orally a capsule of sunflower oil for the duration of the study, ten subjects receive orally a capsule of one of the three SCM's dissolved in sunflower oil every morning at a dose of 0.75 micromoles/kg, and another 10 subjects receive orally a capsule every morning of one of the three SCM's dissolved in sunflower oil at a concentration of 0.375 micromoles/kg.

Qualifications of Subjects

1) Men between the ages of 18 and 55 with a BMI$\geq$28 are eligible.

2) Women between the ages of 18 and 55, whether menopausal, perimenopausal, or post-menopausal, with a BMI$\geq$28.

SUBJECTS EXCLUDED FROM THE STUDY

People who:
a) are hypothyroid,
b) have a known history of possible estrogen receptive positive cancer (breast, ovarian, uterine, testicular),
c) subjects with a history of anorexia or bulimia,
d) subjects with any history of cancer
e) pregnant females
f) nursing females
g) subjects with EKG's indicating tachycardia, old myocardial infarct, angina, or evidence of coronary artery disease.
h) Subjects with a BMI<28.

Appropriate Laboratory Evaluation

Different tests are performed at five different times during each study, namely at the screening of potential participants, at the beginning of the study, weekly during the trials, at the end of the first 4 week period and at the end of the second 4 week treatment period.

1) SCREENING: Subjects are screened to exclude hypothyroidism, pregnancy, and heart disease. The following tests suffice for this: T4, T3, TSH, urine pregnancy test, blood pressure & EKG.

2) BEGINNING OF STUDY: Subjects passing the initial screen are evaluated at the beginning of WEEK #1 as follows:
   a) Estrone, estradiol, and estriol levels, done on the appropriate day of the menstrual cycle in premenopausal females, and without consideration of the time in the menstrual cycle in all other subjects including men. DHEA and testosterone levels are also done.
   b) SMA 20, including glucose, uric acid, and liver function tests
   c) Triglycerides
   d) Cholesterol, including fractions
   e) Glycosolated hemoglobin A1 (HgbA1)
   f) Weight, taken on the same scale each time
   g) Body fat % and total body fat, determined by bioelectrical impedance device. The same instrument must be used on the same patient throughout the study!
   h) Height
   i) Waist and hip measurements 3) WEEKLY ASSESSMENT: body weight, body fat & body fat % by electrical impedance measurement, waist & hip measurements 4) END OF WEEK #5 ASSESSMENT: all labs done at beginning of study, along with blood pressure, TSH and T4, T3 and rT3.

5) END OF WEEK #11: all labs done at beginning of study, but also include EKG.

6) END OF WEEK #13: all labs done at beginning of study.

7) END OF WEEK #18: all labs done at beginning of study

8) END OF WEEK #20: all labs done at beginning of study

Subjects selected to participate in the studies have the following initial measurements:

WEIGHT, WAIST to HIP RATIO, HEIGHT, BMI (calculated), BODY FAT % & TOTAL BODY FAT (via bioelectrical impedance method). Criteria for participation in the studies are listed below.

Study Design

Subjects selected for participation are allowed an ad libetum diet and are given an evaluation sheet to assess their appetite and food intake. Foods excluded include alcohol. Low calorie liquids are stressed in place of high calorie liquids such as fruit juices, milk, sweet tea (tea with sugar), regular soft drinks, coffee with sugar, etc. The importance of drinking 8 glasses of low calorie liquids per day is stressed.

Duration

The study is divided into the following periods:

1. WEEK #1—A DAILY assessment of appetite and food intake is made for one week prior to any medication being issued. This is done by having the patient fill out a hunger questionnaire and by keeping a record of food intake. Food intake record should include amount, type, frequency and time ingested.

2. WEEKS #2, 3, 4, & 5—A four week period where subjects are given a weeks supply of medication at the once weekly weigh-ins. Subjects are split into three groups:

a. One group receives placebo.
b. One group receives an appropriate dose of SCM equal to 0.75 μmol/kg q AM with food.
c. The third group receives an appropriate dose of SCM equal to 0.375 μmol/kg q AM with food.

Ad libetum diets are allowed, and food intake and appetite are assessed daily by the patient with an appropriate questionnaire and booklet. Weekly check-ins for weight and other measurements are done.

3. WEEKS 6 & 7—all subjects are given a drug holiday; weekly revisits for measurements continue.
4. WEEKS 8, 9, 10 & 11—Medication resumes, each group receiving the same medication they received during weeks 2–5.
5. WEEKS 12 & 13—No medication. Just weekly reassessment.
6. WEEKS 14–18—Placebo group only, given 4 weeks of medication in a dose yet to be determined. Weekly assessments to occur as usual.
7. WEEK 18 & 22—Original medication groups are evaluated for weight, body fat and %, and waist measurements.

Subjects are blind to all measurements.

Outcome

This study demonstrates that SCM's 1) reduce appetite, and does so in a dose-dependent manner, and/or 2) produce weight loss, loss of body fat, and/or decrease of body fat % as determined by the various measurements in the study.

EXAMPLE 6

The Effectiveness of Synthesized Combination Molecules (SCM) in Producing Decreased Food Consumption, Weight Loss, and/or Body Fat Loss in Rats when the SCM Consists of a Monounsaturated Fatty Acid Molecule of 20 Carbons or more Joined by an Amide, Ester, or Ether Linkage to a Molecule Containing as Part of its Structure the Perhydrocyclopentanophenanthrene Nucleus Introduction Certain molecules are synthesized by combining two different molecules: 1) a monounsaturated fatty acid molecule of 20 carbon atoms or more, and 2) a molecule whose structure contains a perhydrocyclopentanophenanthrene nucleus or some modification or derivative of a perhydrocyclopentanophenanthrene nucleus, such as a steroid. These new molecules vary as to the connecting bond, which can be an ester, ether, or amide linkage. The resulting synthesized combination molecule (SCM), when taken orally, elicits a decrease in appetite and food intake in mammals, while also producing a loss of body weight and/or body fat.

Subject and Methods

Osborne Mendle rats are selected as the study subjects due to their propensity to gain fat when fed a high fat diet. An initial measurement of body weight is performed on each rat. The rats are placed individually in appropriate cages and allowed an ad libitum diet of standard rat chow and water for a 10-day period. During this 10-day period the rats are gavaged daily with 0.1 cc volume of sunflower oil to allow them to become comfortable with being handled and receiving the gavage tube (it takes about 10 days for this acclimation to occur, and is important so that the animals are not stressed by the gavage).

Daily measurements include the following:
1. Weight
2. Weight of food consumed
3. Spillage
4. Water consumed, both volume and weight The rats remain confined and are denied out-of-cage activity or exercise for the duration of the experiment other than normal daily activity confined to the cage. This initial 10-day period establishes a pattern and average of weight gain, to acclimate the animals to the gavage procedure, and determine the average food and water consumption for each rat.

For the next 28 days, rats receive 0.1 cc volume of either placebo (sunflower oil) or one of several synthesized combination molecules (SCM's) consisting of 1) a monounsaturated fatty acid containing 20 carbon atoms or more, joined to 2) a molecule containing the perhydrocyclopentanophenanthrene nucleus as part of its structure or some modification or derivative of a perhydrocyclopentanophenanthrene nucleus, such as a steroid (such as steroids), in which the linkage between the fatty acid molecule and the molecule containing the perhydrocyclopentanophenanthrene nucleus or some modification or derivative of a perhydrocyclopentanophenanthrene nucleus, is an amide, ester, or ether bond. Specific SCM's tested include synthesized combination molecules (SCM's) consisting of 1) a monounsaturated fatty acid containing 20 carbon atoms or more, joined to one of the following molecules containing the perhydrocyclopentanophenanthrene nucleus or a derivative thereof—either Vitamin D or DHEA (dehydroepiandosterone)—via an amide, ester, or ether bond. Preferred fatty acids used in the SCM include the cis isomers of eicosenoic acid (20 carbon, monounsaturated), docosenoic acid (22 carbon, monounsaturated), and tetracosenoic acid (24 carbon, monounsaturated). Preferred synthesized combination molecules (SCM's) include the fatty acid monoesters in which the fatty acid is made up of either eicosenoic acid, docosenoic acid, or tetracosenoic acid and joined via an ester bond to the steroid estrone (a molecule containing and derived from a perhydrocyclopentanophenanthrene nucleus). Ten rats are assigned to each study group and receive the prescribed SCM simultaneously as follows:

| | |
|---|---|
| FIRST SCM: | the monoester of tetracosenoic acid and cholesterol, a molecule containing the perhydrocyclopentanophenanthrene nucleus |
| SECOND SCM: | the monoether of eicosenoic acid and cholesterol, a molecule containing the perhydrocyclopentanophenanthrene nucleus |
| THIRD SCM: | the monoester of eicosenoic acid and Vitamin D, a molecule containing the perhydrocyclopentanophenanthrene nucleus. |

Rats are assigned to each study group and receive the prescribed SCM as follows:
1. Placebo as sunflower oil, 0.1 cc volume (10 rats/SCM).
2. One of the three SCM's described above, at a dose of 10 micromoles/kg (10 rats/synthesized combination molecule [SCM]).
3. One of the three SCM's described above as described above at a dose of 5 micromoles/kg (10 rats/synthesized combination molecule [SCM]).
4. One of the three SCM's described above as described above at a dose of 3.33 micromoles/kg (10 rats/synthesized combination molecule [SCM]).

5. One of the three SCM's described above as described above at a dose of 2.5 micromoles/kg (10 rats/synthesized combination molecule [SCM]).

The synthesized combination molecule (SCM) preparations to be administered to the rats are prepared by diluting the appropriate weight of each synthesized combination molecule (SCM) in sunflower oil to a standard volume so as to produce the appropriate concentration as noted above for each study group, and so as to allow the prescribed daily dose to equal 0.1 cc.

An appropriate volume of the synthesized combination molecule (SCM) is administered via oral gavage of the appropriate dose each morning for 28 consecutive days. During this 28-day test period, daily measurements continue to be made to determine weight of food consumed, volume and weight of water consumed, and weight change of the rat.

At the end of the study, rats are anesthetized then sacrificed via guillotine. Blood is collected by direct cardiac puncture, and determinations made of the following blood and plasma parameters including a chemistry panel with lipids which includes glucose, triacylglycerols, urea, and insulin. A CBC is also performed. Measurements to determine loss of fat tissue in the rat's fat pad are also performed.

Weight of the uterus is determined. The rats' intestines are then cleaned, the rats are re-weighed, and the whole rat is placed in a blender and made a smooth paste. The paste is used to determine lipid, energy, and water content.

This study shows the efficacy of these SCM in producing 1) a reduction in food consumption, and/or, 2) a reduction of body weight &/or body fat, in a statistically significant manner.

EXAMPLE 7

The Effectiveness of Synthesized Combination Molecules (SCM) in Producing Decreased Food Consumption, Weight Loss, and/or Body Fat Loss in Humans when the SCM Consists of a Monounsaturated Fatty Acid Molecule of 20 Carbons or more Joined by an Amide, Ester, or Ether Linkage to a Molecule Containing as Part of its Structure the Perhydrocyclopentanophenanthrene Nucleus

INTRODUCTION

Certain molecules are synthesized by combining two different molecules: 1) a monounsaturated fatty acid molecule of 20 carbon atoms or more and 2) a steroid molecule. These new molecules vary as to the connecting bond, which can be an ester, ether, or amide linkage. The resulting synthesized combination molecule (SCM), when taken orally, elicits a decrease in appetite and food intake in humans, while also producing a loss of body weight and/or body fat.

Subject and Methods

1. Enlist the required number of subjects who are properly screened to fulfill the necessary qualifications,
2. Perform appropriate laboratory evaluation,
3. Record the various aspects of positive drug response in a manner acceptable for drug approval,
4. Document adverse drug effects, and
5. Perform adequate patient follow-up.

Overview

The study demonstrates that subjects on an ad libitum diet who take a SCM:

1. Experience a decrease in body fat as measured by weight, waist circumference measurements, and/or body fat or body fat % determinations, and
2. Eat less food, and/or
3. Experience decreased appetite.

GENERAL

In this random, double-blind, placebo controlled study, subjects are selected to one of three groups and take a capsule orally every morning containing one of the following: a) sunflower oil (placebo), b) a specific SCM as described above, dissolved in sunflower oil at a dose of 0.75 micromoles/kg, or c) a SCM dissolved in sunflower oil at a dose of 0.375 micromoles/kg.

One of several synthesized combination molecules (SCM's) consisting of 1) a monounsaturated fatty acid containing 20 carbon atoms or more joined to 2) a molecule containing the perhydrocyclopentanophenanthrene nucleus as part of its structure or some modification or derivative of a perhydrocyclopentanophenanthrene nucleus, such as a steroid (such as steroids), in which the linkage between the fatty acid molecule and the molecule containing the perhydrocyclopentanophenanthrene nucleus or some modification or derivative of a perhydrocyclopentanophenanthrene nucleus, is an amide, ester, or ether bond. In this study, three SCM's will be tested simultaneously:

| | |
|---|---|
| FIRST SCM: | the monoester of tetracosenoic acid and cholesterol, a molecule containing the perhydrocyclopentanophenanthrene nucleus as part of its structure |
| SECOND SCM: | the monoester of eicosenoic acid and cholesterol, a molecule containing the perhydrocyclopentanophenanthrene nucleus as part of its structure |
| THIRD SCM: | the monoester of eicosenoic acid and Vitamin D, a molecule containing the perhydrocyclopentanophenanthrene nucleus as part of its structure |

Subjects report weekly for measurements and assessment of any side effects. They are asked to keep a daily record of all food intake, food type, and fluid intake. They are also asked to record any side effects and their frequency (checklist assessment). They are provided with the proper paper work to record these.

Subject Screening and Selection

A total of 90 subjects are selected, randomized and placed in one of three SCM study groups based on the three SCM's above. For each of the three SCM groups, subjects are assigned as follows: ten subjects receive orally a capsule of sunflower oil for the duration of the study, ten subjects receive orally a capsule of one of the three SCM's dissolved in sunflower oil every morning at a dose of 0.75 micromoles/kg, and another 10 subjects receive orally a capsule every morning of one of the three SCM's dissolved in sunflower oil at a concentration of 0.375 micromoles/kg.

Qualifications of Subjects

1) Men between the ages of 18 and 55 with a BMI$\geq$28 are eligible.
2) Women between the ages of 18 and 55, whether menopausal, perimenopausal, or post-menopausal, with a BMI$\geq$28.

Subjects Excluded From the Study

People who:
1) are hypothyroid,
2) have a known history of possible estrogen receptive positive cancer (breast, ovarian, uterine, testicular),
3) subjects with a history of anorexia or bulimia,
4) subjects with any history of cancer
5) pregnant females
6) nursing females
7) subjects with EKG's indicating tachycardia, old myocardial infarct, angina, or evidence of coronary artery disease.
8) Subjects with a BMI<28.

Appropriate Laboratory Evaluation

Different tests are performed at five different times during each study, namely at the screening of potential participants, at the beginning of the study, weekly during the trials, at the end of the first 4 week period and at the end of the second 4 week treatment period.

1) SCREENING: Subjects are screened to exclude hypothyroidism, pregnancy, and heart disease. The following tests suffice for this: T4, T3, TSH, urine pregnancy test, blood pressure & EKG.
2) BEGINNING OF STUDY: Subjects passing the initial screen are evaluated at the beginning of WEEK # 1 as follows:
3) Estrone, estradiol, and estriol levels, done on the appropriate day of the menstrual cycle in premenopausal females, and without consideration of the time in the menstrual cycle in all other subjects including men. DHEA and testosterone levels are also done.
4) SMA 20, including glucose, uric acid, and liver function tests
5) Triglycerides
6) Cholesterol, including fractions
7) Glycosolated hemoglobin A1 (HgbA1)
8) Weight, taken on the same scale each time
9) Body fat % and total body fat, determined by bioelectrical impedance device. The same instrument must be used on the same patient throughout the study!
10) Height
11) Waist and hip measurements
12) WEEKLY ASSESSMENT: body weight, body fat & body fat % by electrical impedance measurement, waist & hip measurements
13) END OF WEEK #5 ASSESSMENT: all labs done in step 2 at beginning of study, along with blood pressure, TSH and T4, T3 and rT3.
14) END OF WEEK #11: same as in #4, but also include EKG.
15) END OF WEEK #13: same as listed in step 4 above.
16) END OF WEEK #18: same as step 5.
17) END OF WEEK #20: same as step 4.

Subjects selected to participate in the studies have the following initial measurements: WEIGHT, WAIST to HIP RATIO, HEIGHT, BMI (calculated), BODY FAT % & TOTAL BODY FAT (via bioelectrical impedance method). Criteria for participation in the studies are listed below.

STUDY DESIGN

Subjects selected for participation are allowed an ad libetum diet and are given an evaluation sheet to assess their appetite and food intake. Foods excluded include alcohol. Low calorie liquids are stressed in place of high calorie liquids such as fruit juices, milk, sweet tea (tea with sugar), regular soft drinks, coffee with sugar, etc. The importance of drinking 8 glasses of low calorie liquids per day is stressed.

DURATION

The study is divided into the following periods:

1) WEEK #1—A DAILY assessment of appetite and food intake is made for one week prior to any medication being issued. This is done by having the patient fill out a hunger questionnaire and by keeping a record of food intake. Food intake record should include amount, type, frequency and time ingested.
2) WEEKS #2, 3, 4, & 5—A four week period where subjects are given a weeks supply of medication at the once weekly weigh-ins. Subjects are split into three groups:
   a. One group receives placebo.
   b. One group receives an appropriate dose of SCM equal to 0.75 $\mu$mol/kg q AM with food.
   c. The third group receives an appropriate dose of SCM equal to 0.375 $\mu$mol/kg q AM with food.

Ad libetum diets are allowed, and food intake and appetite are assessed daily by the patient with an appropriate questionnaire and booklet. Weekly check-ins for weight and other measurements are done.

3) WEEKS 6 & 7—all subjects are given a drug holiday; weekly revisits for measurements continue.
4) WEEKS 8, 9, 10 & 11—Medication resumes, each group receiving the same medication they received during weeks 2–5.
5) WEEKS 12 & 13—No medication. Just weekly reassessment.
6) WEEKS 14–18—Placebo group only, given 4 weeks of medication in a dose yet to be determined. Weekly assessments to occur as usual.
7) WEEK 18 & 22—Original medication groups are evaluated for weight, body fat and %, and waist measurements. Subjects are blind to all measurements.

OUTCOME

This study demonstrates that SCM's 1) reduce appetite in a dose-dependent manner, and/or 2) produce weight loss, loss of body fat, and/or decrease of body fat % as determined by the various measurements in the study.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

What is claimed is:

1. A method of lowering body weight in a mammal comprising administering to said mammal an effective amount of a substantially pure fatty-acid monoester of an estrogen and a fatty acid, wherein the estrogen is selected from the group consisting of estrone, diethyistilbestrol, estriol, estradiol and ethinyl estradiol, the fatty acid is selected from the group consisting of eicosenoic acid, C-22 fatty acid, cis 13 docosenoic acid, and the C-24 fatty acid, cis 15 tetracosenoic acid, in combination with amounts of at least one member selected from the group consisting of pharmaceutically acceptable excipients and cosmetically acceptable excipients in an amount sufficient for the purposes thereof.

2. A method of lowering body weight in a mammal comprising administering to said mammal an effective amount of a monoester of estrone and eicosenoic acid in combination with amounts of at least one member selected from the group consisting of pharmaceutically acceptable excipients and cosmetically acceptable excipients in an amount sufficient for the purposes thereof.

3. A method of lowering body weight in a mammal comprising administering to said mammal an effective amount of the fatty acid monoester of cis 11 cicosenoic acid and estrogen in combination with amounts of at least one member selected from the group consisting of pharmaceutically acceptable excipients and cosmetically acceptable excipients in an amount sufficient for the purposes thereof.

4. The method of claim 1, wherein the estrogen is steroidal and has a steroid ring system with a C-3 position and a hydroxyl group at the C-3 position, the acyl group of the fatty acid is attached to the hydroxyl group at the C-3 position of the steroid ring system in the fatty acid monoester.

5. A method of lowering body weight in a mammal comprising administering to said mammal an effective amount of a substantially pure combination of:

a) a monounsaturated fatty acid molecule of 20 carbon atoms or more; and b) a molecule containing a perhydrocyclopentanophenanthrene nucleus, wherein the fatty acid and the perhydrocyclopentanophenanthrene are linked together, in combination with amounts of at least one member selected from the group consisting of pharmaceutically acceptable excipients and cosmetically acceptable excipients in an amount sufficient for the purposes thereof, wherein the perhydrocyclopentanophenanthrene is an estrogen molecule.

6. A method of lowering bodyweight in a mammal comprising administering to said mammal an effective amount of a substantially pure combination of:

a) a monounsaturated fatty acid molecule of 20 carbon atoms or more; and b) a molecule containing a perhydrocyclopentanophenanthrene nucleus. wherein the fatty acid and the perhydrocyclopentanophenanthrene are linked together, in combination with amounts of at least one member selected from the group consisting of pharmaceutically acceptable excipients and cosmetically acceptable excipients in an amount sufficient for the purposes thereof wherein the substantially pure combination is a substantially pure fatty-acid monoester selected from the group consisting of an estrogen combined with one fatty acid from the group consisting of eicosenoic, docosenoic acid and tetracosenoic acid.

7. The method of claim 5, wherein the substantially pure combination is of:

a) a monounsaturated fatty acid molecule of 20 carbon atoms or more, and b) asteroid; wherein the steroid and fatty acid are linked together.

8. The method of claim 7, wherein the monounsaturated fatty acid molecule of 20 carbons or more is selected from the group consisting of cis isomers of eicosenoic acid, docosenoic acid, and tetracosenoic acid.

9. The method of claim 7, wherein the linkage is via an ester bond.

* * * * *